United States Patent [19]
Verrier et al.

[11] Patent Number: 5,902,250
[45] Date of Patent: May 11, 1999

[54] HOME-BASED SYSTEM AND METHOD FOR MONITORING SLEEP STATE AND ASSESSING CARDIORESPIRATORY RISK

[75] Inventors: Richard L. Verrier, Wellesley; J. Allan Hobson, Brookline; Eric G. Lovett, Framingham; Edward F. Pace-Schott, Ipswitch, all of Mass.

[73] Assignees: President and Fellows of Harvard College, Cambridge; Beth Israel Deaconess Medical Center, Inc., Boston, both of Mass.

[21] Appl. No.: 08/828,633

[22] Filed: Mar. 31, 1997

[51] Int. Cl.$^6$ .................................................. A61B 5/0205
[52] U.S. Cl. ............................................ 600/515; 600/513
[58] Field of Search .................................. 600/481, 483, 600/509, 513, 515, 484, 529

[56] References Cited

U.S. PATENT DOCUMENTS

| | | | |
|---|---|---|---|
| 4,757,815 | 7/1988 | Strandberg | 600/529 |
| 4,805,629 | 2/1989 | Farges | 600/484 |
| 4,836,219 | 6/1989 | Hobson et al. . | |
| 5,101,831 | 4/1992 | Koyama et al. | 600/529 |
| 5,148,812 | 9/1992 | Verrier et al. . | |
| 5,187,657 | 2/1993 | Forbes . | |
| 5,265,617 | 11/1993 | Verrier et al. . | |
| 5,269,326 | 12/1993 | Verrier . | |
| 5,280,791 | 1/1994 | Lavie | 600/509 |
| 5,437,285 | 8/1995 | Verrier et al. . | |
| 5,560,370 | 10/1996 | Verrier et al. . | |
| 5,566,067 | 10/1996 | Hobson et al. . | |

OTHER PUBLICATIONS

"Nightcap: Laboratory and Home–Based Elevation of a Portable Sleep Monitor"; O. Ajilore et al; Psychophysiology vol. 32; 1995; pp. 92–98.

"Sleep–Related Cardiovascular Risk: New Home–Based Monitoring Technology for Improved Diagnosis and Therapy"; R.L. Verrier et al.; Ann Noninvas Electrocardiology, vol. 2 No. 2; Apr. 1997; pp. 158–175.

"Sleep Patterns in the Intensive Care Unit and on the Ward After Acute Myocardial Infarction"; R. Broughton et al.; Electroencephalography and Clinical Neurophysiology 45; 1978; pp. 348–360.

"Primary Coronary Vasodilation Associated with Pauses in Heart Rhythm During Sleep"; L.W. Dickerson et al.; American Journal Physiol 264; 1993; pp. R186–R196.

"Relationship Between Coronary Hemodynamic Changes and the Phasic Events of Rapid Eye Movement in Sleep"; L.W. Dickerson et al.; Sleep 16(6); 1993; pp. 550–557.

"Sinus Arrest During REM Sleep in Young Adults"; C.P. Guilleminault et al; New England Journal of Medicine vol. 311 No. 16; 1984; pp. 1006–1010.

"Association of Sleep Apnoea with Myocardial Infarction in Men"; J. Hung et al.; The Lancet vol. 336; 1990; pp. 261–264.

(List continued on next page.)

*Primary Examiner*—William E. Kamm
*Assistant Examiner*—George R. Evanisko
*Attorney, Agent, or Firm*—Wolf, Greenfield & Sacks, Inc.

[57] ABSTRACT

A method for determining the sleep state of a patient includes monitoring heart rate variability of the patient and determining sleep state based on the heart rate variability. The method also may include monitoring the frequency of eyelid movements and making the sleep state determination based also on the frequency of eyelid movements. A method for determining respiratory pattern includes monitoring heart rate variability by receiving heart beat signals and determining respiratory pattern from the strength of the signals. A home-based, wearable, self-contained system determines sleep-state and respiratory pattern, and assesses cardiorespiratory risk, of a patient based on the frequency of eyelid movements, the frequency of head movements, and heart rate variability of the patient.

7 Claims, 9 Drawing Sheets

OTHER PUBLICATIONS

"Differential Effects of Sleep State on Coronary Hemodynamic Function"; D.A. Kirby et al.; American Journal Physiol 256 (Heart Circ Physiol 25); 1989; pp. H1378–H1383.

"Differential Effects of Sleep State on Coronary Hemodynamic Function During Stenosis"; D.A. Kirby; et al.; Physiology and Behavior vol. 45; 1989; pp. 1017–1020.

"Nonuniform Nighttime Distribution of Acute Cardiac Events: A Possible Effect of Sleep States"; C.E. Lavery et al; Circulation in Press; Jul. 1997; pp. 1–32.

"Autonomic Modulation of the Cardiovascular System During Sleep"; G. Mancia; The New England Journal of Medicine vol. 328 No. 5; 1993; pp. 347–349.

"Paroxysmal Ventricular Tachycardia During Repeated 24–Hour Ambulatory Electrographic Monitoring of Post–myocardial Infarction"; M. Moller et al.; Br Heart Journal 43; 1980; pp. 447–453.

"Timing of Sudden Death in Patients with Heart Failure"; D.K. Moser et al.; Journal of American College Cardiol vol. 24 No. 5; Oct. 1994; pp. 963–967.

"Sudden Death in Sleep of Leotian–Hmong Refugees in Thailand; A Case–Control Study"; R.G. Murger; American Journal of Public Health vol. 77 No. 9; Sep. 1987; pp. 1187–1190.

"The Association of Nocturnal Angina Pectoris with Dreaming"; J.B. Nowlin et al.; Annals of Internal Medicine vol. 63 No. 6; 1965; pp. 1040–1046.

"Ventricular Fibrillation Causes Sudden Death in Southeast Asian Immigrants"; C.M. Otto et al.; Annals of Internal Medicine vol. 100 No. 1; Jul. 1984; pp. 45–47.

"The Onset of Symptomatic Atrial Fibrillation and Paroxysmal Supraventricular Tachycardia is Characterized by Different Circadian Rhythms"; C. Rostagno et al.; Amer J. Cardiol vol. 71; 1993; pp. 453–455.

"Long QT Syndrome Patients with Mutations of the SCN5A & HERG Genes Have Differential Responses to Na+Channel Blockade . . ."; P.J. Schwartz et al.; Circulation vol. 92 No. 12; 1995; pp. 3381–3386.

"Sympathetic–Nerve Activity During Sleep in Normal Subjects"; V.K. Somers et al.; New England Journal of Medicine vol. 328 No. 5; Feb. 1993; pp. 303–307.

"Heart Rate Variability During Specific Sleep Stages; A Comparison of Healthy Subjects with Patients After Myocardial Infarction"; E. Vanoli et al.; Circulation vol. 91 No. 7; Apr. 1995; pp. 1918–1922.

Cardiovascular Research "Sleep, dreams, and sudden death; the case for sleep as an autonomic stress test for the heart." Cardiovascular Research 31 (1996) pp. 181–211, Richard L. Verrier et al.

Committee Report Methodological Guidelines for Impedance Cardiography, A. Sherwood et al., Psychophysiology vol. 27, No. 1, Jan., 1990, pp. 1–23.

The Technique of Impedance Cardiography, H.H. Woltier et al., Eur. Heart J. vol. 18, Sep. 1997, pp. 1396–1403.

From the data, an estimated 300,000 nocturnal myocardial infarctions and 37,500 nocturnal sudden deaths occur yearly in the U.S. The latter figure is approximately equal to 88% of the number of deaths due to automobile accidents and is approximately 50% greater than the number of deaths due to HIV infection. Sudden death during sleep often victimizes infants and adolescents, and adults with ischemic heart disease, who have a median age of 59.

HOME-BASED SYSTEM AND METHOD FOR MONITORING SLEEP STATE AND ASSESSING CARDIORESPIRATORY RISK

FIELD OF THE INVENTION

The present invention relates generally to systems and methods for monitoring sleep state and assessing cardiorespiratory risk and, more particularly, to a simple, yet accurate, self-contained, wearable system and method for monitoring sleep state and assessing cardiorespiratory risk particularly suited for home use.

BACKGROUND OF THE INVENTION

Sleep often affects healthy individuals differently from those with heart and/or respiratory ailments. In healthy individuals, sleep generally exerts a salutary and restorative influence. In patients with respiratory and/or heart ailments, by contrast, sleep may bring on breathing disorders, myocardial ischemia, arrhythmias, and even death. Two main factors thought to be responsible for such reactions are sleep-state dependent changes in autonomic activity and depression of respiratory control mechanisms.

Sleep states include rapid eye movement (REM) state and non-REM, or slow wave sleep (SWS) state. The brain, in serving its needs for periodic reexcitation during REM sleep state and dreaming, may impose significant demands on the heart by inducing bursts of sympathetic activity which may, in susceptible individuals, compromise coronary blood flow and trigger life-threatening arrhythmias. During SWS state, hypotension may lead to under-perfusion of the heart and brain as a result of a lowered pressure gradient through stenosed blood vessels. Also, impairment of breathing ventilation during sleep by obstructive sleep apnea may cause reductions in arterial oxygen saturation. These conditions may be worsened by cardiac medications which cross the brain-blood barrier, altering sleep structure and possibly leading to nightmares with severe cardiac autonomic discharge.

Patients with coronary artery disease face nocturnal health risks. Approximately 25% of cases of first manifestations of underlying coronary artery disease include catastrophic events such as myocardial infarction and sudden death due to respiratory or cardiac distress during sleep. In a recent study, it was observed that approximately 20% of myocardial infarctions and 15% of sudden deaths occur during the period between midnight and 6:00 A.M. Such a non-uniform distribution of myocardial infarctions and sudden deaths suggests that sleep-state dependent fluctuations in autonomic nervous system activity may have precipitated a significant number of the events.

Different pathophysiologic mechanisms are responsible for nocturnal death in different age groups and among different patient groups. Disturbed respiration during sleep is particularly dangerous for patients with heart-related and certain other ailments. Respiratory apnea, for example, which afflicts approximately 1.5 million Americans, may bring on hypertension, myocardial infarction and sudden death, particularly in individuals with ischemic heart disease. Patients with heart failure, those with warning signs of Sudden Infant Death Syndrome (SIDS), pause dependent long QT syndrome or Sudden Unexplained Nocturnal Death Syndrome (SUNDS) (which primarily affects young Southeast Asian men) also are at particularly high risk for dangerous nocturnal cardiorespiratory events. Mobile coronary care unit reports indicate a higher nighttime incidence of atrial fibrillation and arrhythmia which is responsible for significant morbidity and mortality.

Because of the known risks associated with sleep in patients with cardiac ailments and other health problems, monitoring sleep state and respiratory pattern in conjunction with synchronized cardiac monitoring, would aid in the treatment of such patients. Particularly, such monitoring would aid in the diagnosis of ailments, would offer specific information on particular patients' sleep state-dependent cardiac response, and would help in the prevention of dangerous nocturnal cardiac events. Additionally, because certain cardiac medicines, particularly those which cross the brain-blood barrier, affect heart function in often unknown and sometimes dangerous ways during sleep, monitoring sleep state in conjunction with cardiac response would aid in the selection of appropriate medicines and dosages.

Despite the known risks associated with sleep in certain individuals, however, sleep state monitoring has not been an integral component of cardiac patient care, largely because hospital-based or ambulatory monitoring sleep studies are complex and expensive and also because simple, yet accurate, equipment for monitoring sleep and heart function in the familiar home environment is not available.

Hospital-based systems are the most accurate for monitoring sleep state. One such system provides detailed information about and individuals brainwave activity through electroencepholographic (EEG) signals, eyelid movement through electrooculographic (EOG) signals, and muscle tone through electromyographic (EMG) signals. An electrocardiogram also provides information on heart function through electrocardiographic (ECG) signals. Typically, arterial blood pressure, respiration, oxygen saturation, and body movements also are recorded with hospital-based systems. The recorded events are temporally synchronized for later analysis and study.

Notwithstanding its thoroughness, there exist a number of drawbacks with the hospital-based system. The procedure is disruptive to a patient's sleep as it requires the patient to wear multiple scalp electrodes, a blood pressure cuff and respiratory recording devices. It also is disruptive to the patient's sleep because it is conducted in an unfamiliar environment. As a result, a highly disruptive "first night" effect occurs, which includes sleep that is lighter and more fragmented than usual and which may last up to 12 consecutive days. The results obtained, therefore, may not accurately reflect what will occur when the patient is released from the hospital. Another significant limitation to the hospital-based system is the cost of use as it requires a trained technician and sleep scorer to operate. Moreover, it includes sophisticated and expensive equipment and it requires a hospital stay for the patient.

The field approach equivalent, which best approaches the accuracy and thoroughness of the hospital-based system, is the system used in ambulatory polysomnography (PSG). The ambulatory PSG system is a portable system available for home-based use that includes surface electrodes connected to the scalp, eye and body. A portable recorder receives and records EEG, EOG, ECG and EMG signals. Portable equipment also exists for measuring respiration, oxygen saturation, temperature and body movement. All signals are temporally synchronous and, like the hospital-based system, are recorded first and then analyzed.

While the ambulatory PSG system has the advantage over the hospital-based system that it may be used in the familiar home environment and it appears to reveal a reduction in first night effects, it also suffers from a number of drawbacks. For example, the system may negatively affect sleep quality due to the bulk and weight of the recorders and the need for multiple scalp and body electrodes. Additionally, a technician is required to apply the electrodes and the data produced is complex, thus requiring analysis of such data by trained personnel, adding significantly to the cost of its use.

U.S. Pat. No. 5,187,657 to Forbes, titled Cardiac Analyzer with REM Sleep Detection, discloses a home-based system for monitoring sleep state and cardiac function, much like the PSG system. The system disclosed uses sleep state sensors to detect eyelid movement, and muscle tone or brain wave activity, from which sleep state is inferred. When REM state is detected, then recording of ECG and other signals is initiated. Cardiac events attributable to SWS state phenomena or to disturbed respiration are thus not monitored.

In each of the hospital-based and ambulatory PSG systems, as well as in the system disclosed in the Forbes patent, sleep state is determined as a function of eyelid and/or head movement but not as a function of heart function. The accuracy of sleep state data therefore is limited. Additionally, the hardware required for measuring respiratory pattern is separate from the other equipment and, therefore, adds to the expense and may further disrupt sleep quality.

A more simple sleep state monitoring device available for home use is described in U.S. Pat. No. 4,836,219 to Hobson, titled Electronic Sleep Monitor Headgear, and owned by the President and Fellows of Harvard College, which patent is incorporated by reference herein in its entirety. The Hobson patent is licensed to Healthdyne which sells the device under the name Nightcap. The Nightcap device includes a piezoelectric sensor that attaches to the eyelid of a patient and a tilt sensor connected to a headband worn by the patient. The eyelid sensor and tilt sensor provide electronic signals respectively representative of eyelid movements and head movements to recording circuitry through electric wires. Sleep state is determined based on the eyelid and head movement information.

While the Nightcap is available for home use, it requires the patient to wear a headband which may negatively affect the sleep quality of the patient. Also, the Nightcap device is limited to monitoring sleep state; it does not also monitor heart function, for example.

None of the prior art systems discussed above provide a simple, self-contained, home-based system that assesses sleep-related cardiorespiratory risk.

Accordingly, one object of the present invention is to provide a simple system and method for assessing cardiorespiratory risk that is available for home use and which minimally affects sleep quality.

SUMMARY OF THE INVENTION

Applicants have discovered a relationship between heart function and sleep state. To improve the accuracy of sleep state monitoring, in one embodiment of the invention, Applicants have taken advantage of the discovered relationship by using heart function information in determining sleep state.

This embodiment of the invention is directed to a method of determining sleep states of a patient. The method comprises the steps of: monitoring heart rate variability of the patent; and dynamically determining the sleep state of the patient based on the heart rate variability.

In an embodiment, the method also includes monitoring the frequency of eyelid movements of the patient. In this embodiment, the sleep state determination also is based on the frequency of eyelid movements.

In an embodiment, the method further includes monitoring a frequency of head movements of the patient. In this embodiment, the sleep state determination is based also on the frequency of head movements.

In an embodiment of the invention, monitoring the frequency of eyelid movements includes applying an eyelid sensor to the eyelid of the patient, which eyelid sensor produces an eyelid movement signal each time the eyelid moves.

In an embodiment, monitoring heart rate variability includes determining chest wall impedance of the patient. In this embodiment, the method further includes monitoring breathing pattern of the patient from the frequency of eyelid movements and from heart rate variability.

In an embodiment of the invention, monitoring heart rate variability includes applying at least one heart sensor to a chest wall of the patient, which heart sensor produces a heart beat signal each time the heart beats.

In an embodiment of the invention, the method further includes temporally synchronizing the heart beat signals with the eyelid movement signals.

In an embodiment of the invention, an alarm is provided if a dangerous breathing pattern or heart rate is detected.

Applicants also have discovered that ECG signals have at least one characteristic related to respiratory pattern. Another embodiment of the invention, therefore, is directed to a method for determining the breathing pattern of a patient based at least in part on ECG signals. The method comprises the steps of: monitoring a heart rate of the patient with heart rate variability signals; and determining the breathing pattern based on the strength of the heart rate variability signals.

In an embodiment, the method further includes monitoring a frequency of eyelid movements and determining the breathing pattern based also on the frequency of eyelid movements.

A further embodiment of the invention is directed to a home-based, self-contained, wearable processing system that minimally affects sleep quality, if at all. The system includes an eyelid sensor, applied to an eyelid of the patient, that produces eyelid signals representing eyelid movements. A head movement sensor, applied to the head of the patient, produces head signals representing head movements. At least one heart sensor, applied to the chest wall of the patient, produces heart beat signals representing heart beats. A processor temporally synchronizes, records and analyzes the eyelid, head and heart beat signals to assess cardiorespiratory risk.

In an embodiment, the processor also determines the sleep state of the patient based on the eyelid, head and heart beat signals.

In an embodiment, the processor also monitors a breathing pattern of the patient based on the heart beat signals.

In an embodiment, the system further includes an alarm that is triggered when a dangerous cardiorespiratory state is detected.

DETAILED DESCRIPTION

Figure 1:
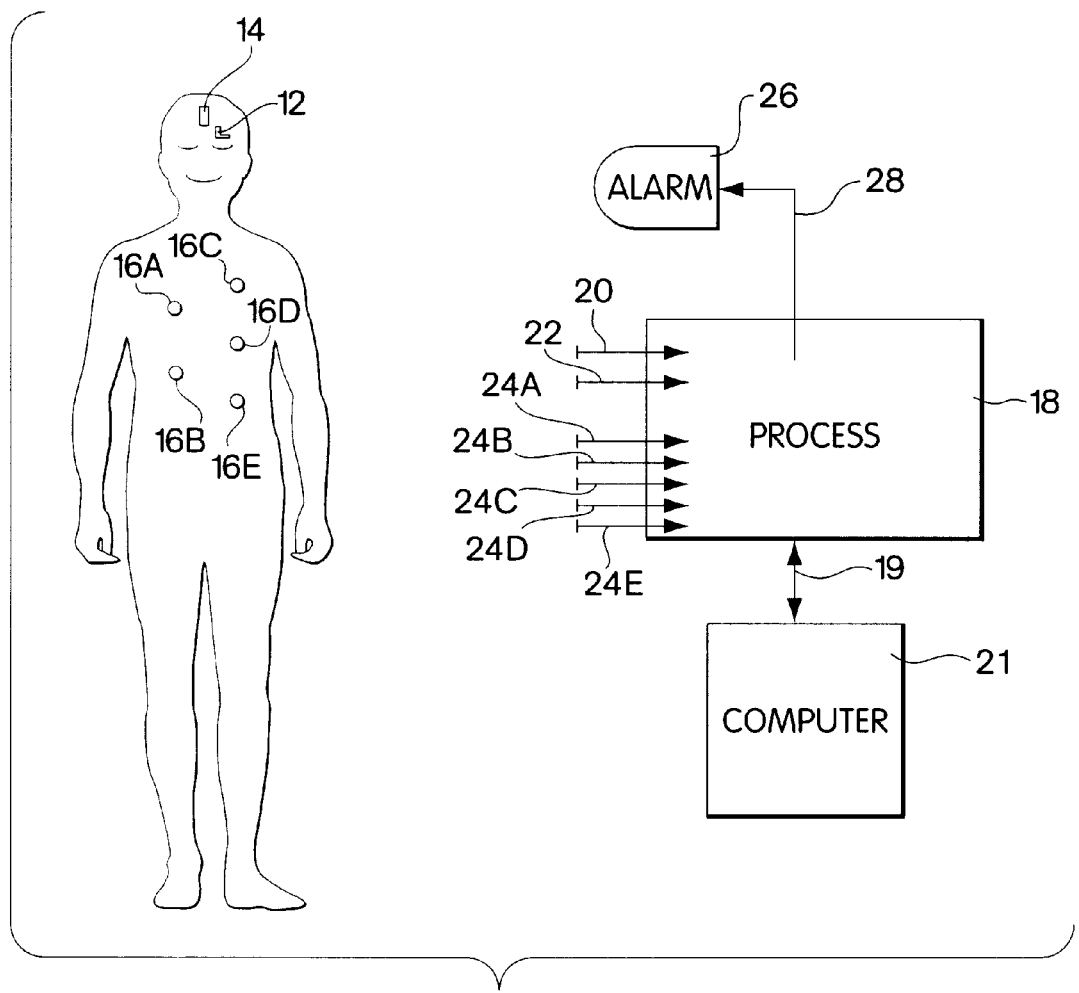
FIG. 1 is a general block diagram of one embodiment of the home-based system according to the invention.

FIG. 1 is a block diagram of one embodiment of a home-based system that monitors sleep state and/or respiratory pattern, according to the invention. As shown, the system includes multiple sensors attached to the body of a patient 10. The sensors include: sensor 12, attached to the eyelid of patient 10, for monitoring eyelid movements; sensor 14, attached to the head (preferably forehead of patient 10) for monitoring head movements; and at least one sensor 16 (five sensors 16A–16E are shown in this exemplary embodiment), attached to the chest wall of patient 10, for monitoring heart rate and function. Analog electrical signals produces by the sensors are provided (either through electrical wires or transmitted through the air) to a portable processing unit 18 which synchronizes, processes and records such signals. In accordance with a first processing scheme described below, unit 18, very accurately monitors sleep state. In accordance with another processing scheme described below, unit 18 monitors respiratory pattern.

Processor 18 may be coupled to an external computer 21 through bi-direction bus 19 so that the data received and processed by processor 18 can be stored, manipulated and further analyzed within external computer 21. Additionally, as will be described in greater detail below, inputs can be received by processor 18 from computer 21 through bus 19 to alter the schemes for monitoring sleep state and/or respiratory pattern. The inputs may, for example, be related to specific predetermined data on a particular patient.

Optionally, an external alarm 26 may be coupled to processor 18 through line 28 such that, upon detection of a dangerous cardiorespiratory state such as a heart arrhythmia or a respiratory apnea, an alarm signal is issued to awaken the patient. This may occur by processor providing a control signal through line 28 to alarm 26 causing alarm 26 to issue such a signal. Alarm 26 may, for example, be a speaker that issues an audible alarm signal. Other alarms may be used alternatively.

Advantages of the system include its simplicity, ease of use, accuracy and thoroughness. The system can be used at home. The system is self-contained and only a minimal number of sensors are required to be worn by the patient. As a result, sleep quality is minimally affected, if at all. In addition, the electrodes can be self-placed quite easily by the patient. Also, the system is quite user-friendly; a technician is not required to analyze data. Further, because both heart function data and head and eyelid movement data are used to determine sleep state and respiratory pattern, very accurate determinations result. Finally, in one embodiment, an alarm system is included for awakening the patient if a dangerous cardiorespiratory state such as a heart arrhythmia or a breathing apnea is detected.

As shown in FIG. 1, sensor 12 provides electrical signals representing eyelid movements to input 20 of unit 18. Sensor 14 provides electrical signals representing head movements to input 22 of unit 18. Sensors 16A–16E respectively provide ECG signals to inputs 24A–24E. For ease of illustration and discussion, inputs 24A–24E are referred to collectively as input 24. The signals may be analog signals conventionally provided along electric wires (not shown) connected between the sensors and the inputs. Alternatively, the sensors may be transmitted by transmitters (not shown), electrically connected to the sensors, and received by receivers (also not shown), electrically connected to the inputs of unit 18.

Sensor 12 preferably is a piezoelectric sensor. Such a sensor is commercially available under the name Nightwatch™ from Healthdyne Technologies Company of Marietta, Ga. The piezoelectric sensor generates an analog voltage in response to mechanical force or deformation of the sensor. Deformation of the sensor is caused by movement of the eyelid. The amplitude of the voltage generated depends on the strength of the eyelid movement, wherein a stronger eyelid movement causes the provision of a greater amplitude voltage.

The signals produced by sensor 12 are received by processor 18 through input 20. Processor 18 monitors the frequency of electric signals received having a signal strength (voltage amplitude) above a threshold voltage level corresponding to a passive eyelid movement (defined below). The threshold voltage can be preprogramed and can depend on a particular subject or group of subjects.

Sensor 12 preferably is a piezoelectric sensor that includes two strips (not shown) of piezoelectric film material which are adhesively attached to one another in an electrically differential arrangement. The strips include respective eyelid mounting rectangles (also not shown) and strip portions (also not shown). The strip portions are physically spaced and electrically insulated from one another. One surface of the eyelid mounting rectangle of the piezoelectric sensor preferably is placed on the eyelid of a subject between the eyelash and eyebrow. The piezoelectric sensor film is very lightweight and is not cumbersome for the patient 10. The sensor also is sufficiently sensitive to produce detectable output voltages in response to passive eyelid movements.

The sensor preferably is attached using adhesive and can include an adhesive backing that is exposed by peeling away a laminate layer from one surface of the rectangle portion of the sensor. The rectangle portion of the sensor preferably falls within the size range of 1 mm by 4 mm to 5 mm by 12 mm. Such a piezoelectric sensor is described in detail, for example, in U.S. Pat. No. 5,566,067 to Hobson et al., titled Eyelid Vigilance Detector System, owned by the President and Fellows of Harvard College, which patent is herein incorporated by reference in its entirety. While use of a piezoelectric sensor is preferable, other sensors that are sensitive enough to produce accurate and detectable electric signals in response to passive eyelid movements are suitable.

Eyelid movements generally fall into three categories: (1) "large active" or significant eyelid movements such as blinks; (2) "small active" eyelid movements which are substantially less significant movements than large active eyelid movements, such as twitches; and (3) "passive" eyelid movements, which are less significant movements than small active eyelid movements and which are caused by movements of the eyeball underneath the eyelid. Small active eyelid movements are caused by involuntary twitches of the eyelid muscle when the muscle maintains the eyelid open in response to neuronal signals received from the brain. Passive eyelid movements are caused when the eyeball moves beneath a closed eyelid, which typically occurs while a person is sleeping, most often during REM sleep state. As used herein, "eyelid movements" refer to large active, small active and passive eyelid movements.

Sensor 14 preferable is a tilt switch or other sensor that detects movements of the head of patient 10 from a reference position. The signals may have an amplitude or other characteristic (such as frequency) that represents the displacement of the head from the reference position. Alternatively, the sensor can be calibrated such that a constant signal is produced any time the head moves a predetermined distance from a reference position. Mercury tilt switches are available for such use.

Like sensor 12, sensor 14 can be adhesively attached to the forehead of patient 10 by removing a laminate layer that covers an adhesive layer. Alternatively, sensor 14 can be attached to the forehead of patient 10 using medical tape, an adhesive strip or a headband. Any attachment mechanism that would retain sensor 14 to the head of patient 10 during sleep related movements is suitable.

Sensors 16A–16E may be conventional ECG electrodes and may be placed in spaced relation on the chest wall of patient 10 such that they can detect heart beats. Such electrodes may be placed on the chest wall using an adhesive paste. A suitable electrode is a soft, flexible, adhesive patch approximately the size of a U.S. fifty cent coin and is prepasted on one side with electrically conductive gel. Marquette Electronics, Inc. of Milwaukee, Wis., manufactures a suitable electrode.

Figure 2:
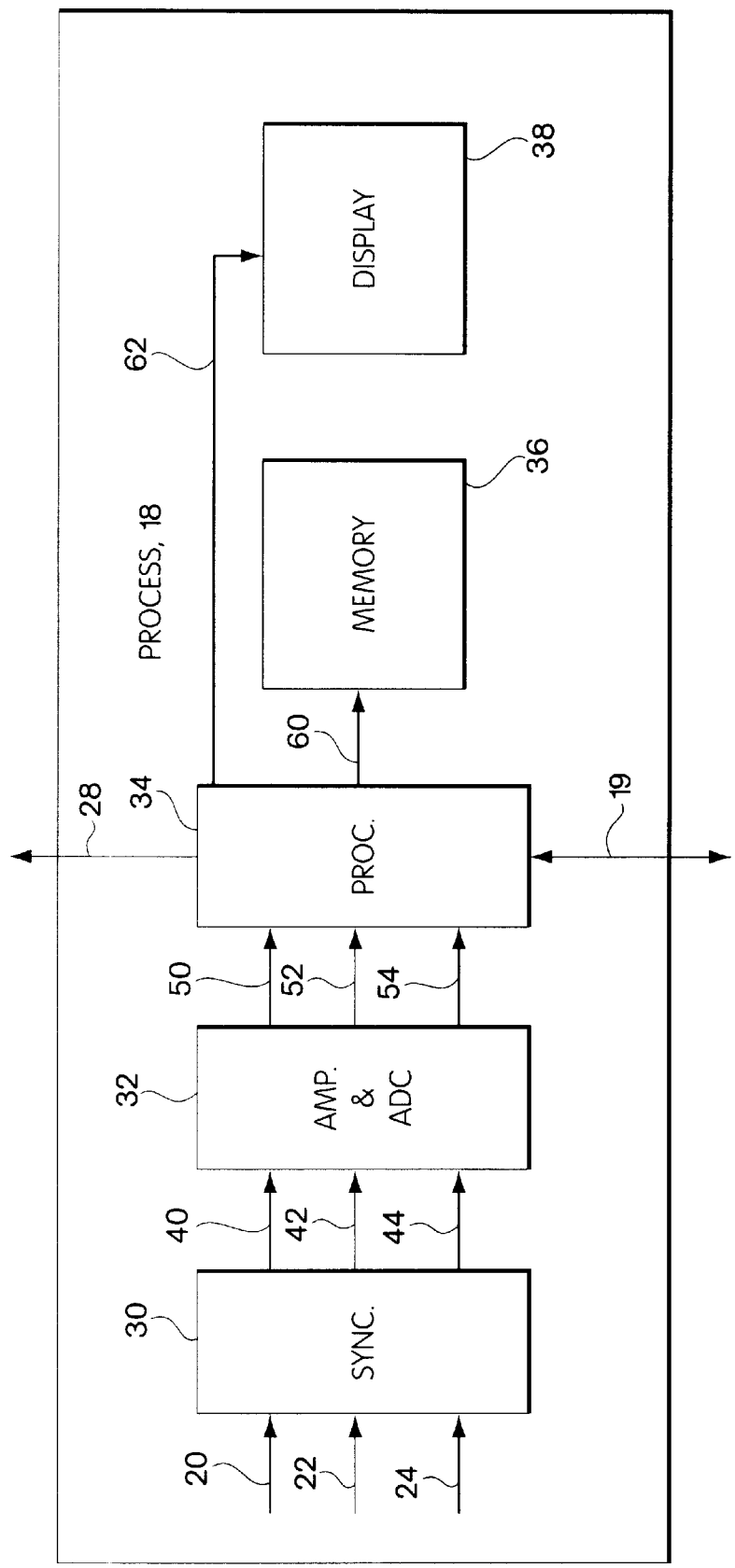
FIG. 2 is a more detailed block diagram of one embodiment of the process unit of the system of FIG. 1.

FIG. 2 is a more detailed block diagram of the components of processor 18 according to one embodiment of the invention. As shown, processor 18 includes a synchronization circuit 30, an amplifier and filter circuit 32, a processor 34, a memory 36 and a display 38. In operation, synchronization circuit 30 receives eyelid movement signals on input 20, head movement signals on input 22 and ECG signals on input 24. Synchronization circuit temporally synchronizes such signals. Synchronization circuit 30 preferably is an analog and/or digital signal processing circuit that performs the synchronization function but can be any circuit for performing that function.

Once temporally synchronized, the eyelid movement, head movement and ECG signals are provided respectively on lines 40, 42 and 44 to amplification and filtering circuitry 32. Preferably, amplification and filtering circuitry 32 amplifies such signals and filters such signals to reduce noise outside of a frequency band of interest. In one embodiment, the analog signals also may be converted to digital signals by conventional analog-to-digital converter circuits included within circuitry 32, such that downstream processing is performed digitally. Digital processing typically is more straightforward than analog processing.

Circuitry 32 may include conventional analog amplification circuitry such as operational amplifiers and conventional filtering circuitry such as analog or digital filters; the filtering may be performed in the analog domain and/or in the digital domain. The signals may be amplified, filtered and converted by separate amplification, filtering and conversion circuitry or may be amplified, filtered and converted by the same circuitry, performed in a pipelined fashion.

Eyelid movement, head movement and ECG signals preferably are provided along lines 50, 52 and 54, respectively, to processor 34. Processor 34 processes the signals in accordance with schemes described in detail below. In one embodiment, processor 34 implements a scheme to monitor sleep states of patient 10. In another embodiment, processor 34 monitors the breathing rhythm of patient 10.

The processed signals may be provided in analog and/or digital format along a line or bus 60 to memory 36. Memory 36 may be any conventional memory element, analog or digital, such as a tape, disk, etc. Additionally, the processed signals and/or a user-readable sleep state, respiratory pattern and/or heart function report may be provided along bus 62 to display 38. Display 38 may be any conventional display from which an image, graph, or other information may be read.

Processor 34 preferably is a microprocessor which runs software to implement the schemes described below. The software can be written in any conventional software programming language such as C++, or other. The microprocessor can receive inputs along bus 19 to alter the schemes in accordance with data or predetermined knowledge of a particular patient, such as knowledge of the patient's medical history, sleeping habits, etc. For example, if a patient has had a myocardial infarction, then the thresholds for determining sleep state and for alarming the patient may be different than those for a patient without a known heart-related ailment. Additionally, knowledge of the patient's sleeping habits such as whether the patient snores may also alter the thresholds.

In one embodiment, processor 34 analyzes at least some of the input signals and determines whether the patient is in REM sleep state, SWS sleep state or quiet wakefulness. Alternate schemes for making this determination are described below with reference to FIGS. 5 and 6. In another embodiment, a scheme is implemented by processor 34 for monitoring the breathing pattern of the patient based on the ECG signals. Such a scheme is described below with reference to FIG. 8. In a further embodiment, a scheme is implemented by processor 34 to monitor sleep state, breathing rhythm and heart function, and to provide an alarm if a dangerous condition is detected. Such a scheme is described below with reference to FIG. 9.

It should be understood that while processor 34 is shown and described herein as a digital processor which runs software for implementing the schemes described below, processor 34 alternatively could be any digital and/or analog circuit that performs the functions of the schemes described below. For example, in the embodiment in which processor 34 analyzes head movement and eyelid movement input signals to aid in sleep state determination (FIG. 6), processor 34 could include circuitry described, for example, in U.S. Pat. No. 4,836,219 to Hobson et al., titled Electronic Sleep Monitor Head Gear, owned by the President and Fellows of Harvard College, which patent is herein incorporated by reference in its entirety. In the Hobson '219 patent, FIG. 2 shows analog circuitry for receiving and processing head movement and eyelid movement signals to determine sleep state. As described below, in the present invention, ECG signals are processed, either alone (in the embodiment described with reference to FIG. 5) or in combination with eyelid movement and head movement signals (in the embodiment described with reference to FIG. 6), to determine sleep state.

Through the received ECG signals, heart function is also is monitored by the system of the invention. Cardiac electrical stability can be assessed by analyzing at least one of a beat-to-beat alternation in a T-wave of an ECG signal or dispersion of a repolarization in the ECG signal. Provocation of cardiac electrical instability by autonomic nervous system activity is achieved by simultaneous analysis of heart rate variability. Such analysis of cardiac electrical instability, with or without simultaneous analysis of autonomic nervous system regulation, is disclosed in the following U.S. patents, all of which are incorporated by reference herein there entirety: (1) U.S. Pat. No. 5,437,285 to Verrier et al., titled Method and Apparatus for Prediction of Sudden Cardiac Death by Simultaneous Assessment of Autonomic Function and Cardiac Electrical Stability; (2) U.S. Pat. No. 5,265,617 to Verrier et al., titled Methods and Means for Non-Invasive Dynamic Tracking of Cardiac Vulnerability by Simultaneous Analysis of Heart Rate Variability and T-Wave Alternans; (3) U.S. Pat. No. 5,560,370 to Verrier et al., titled Method and Apparatus for Prediction of Cardiac Electrical Instability by Simultaneous Assessment of T-Wave Alternans and QT Interval Dispersion; and (4) U.S. Pat. No. 5,148,812 to Verrier et al., titled Non-Invasive Dynamic Tracking of Cardiac Vulnerability by Analysis of T-Wave Alternans.

Figure 3:
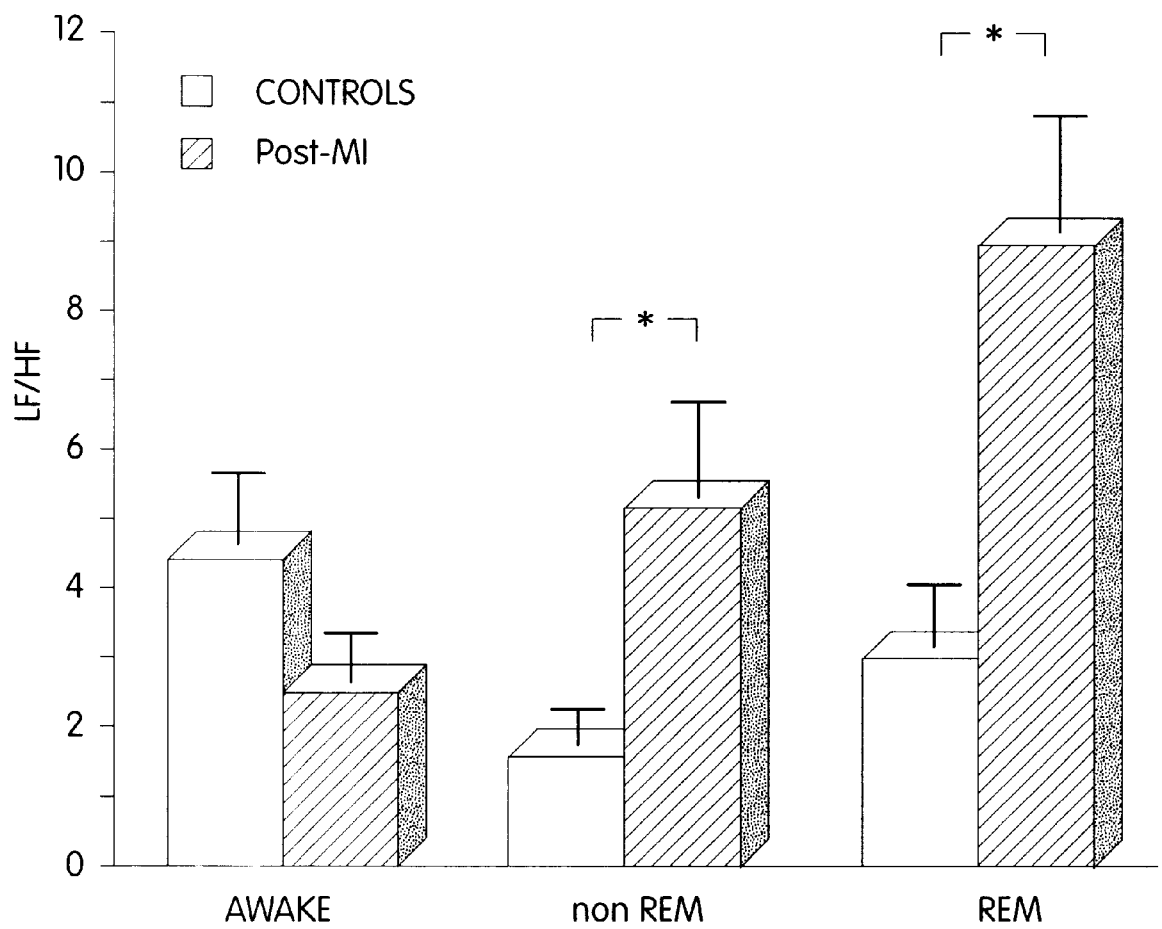
FIG. 3 is a graph illustrating typical low frequency/high frequency (LF/HF) heart rate variability ratios for awake and sleep states.

It is known that the frequency of eyelid movements and the frequency of head movements differ during different sleep states. Applicants herein have discovered that heart rate variability ratios also differ according to sleep state. Shown if FIG. 3 is a graph illustrating this point. The vertical axis of of the graph includes the LF/HF heart rate variability ratio, commonly computed and observed in electrocardiogram systems. One such system for computing the ratio is a portable device known as the Holter device.

Shown across the horizontal axis are different states including quiet wakefulness (awake), non-REM or SWS sleep state, and REM sleep state. For each, shown are the LF/HF ratio for a healthy patient and that for a patient who has suffered a myocardial infarction. As shown, in quiet wakefulness, a healthy patient has an LF/HF ratio of approximately 4.5 whereas a post-myocardial infarction patient has an LF/HF ratio of approximately 2.5. In SWS sleep state, a healthy patient has an LF/HF ratio of approximately 1.5 whereas a post-myocardial infarction patient has an LF/HF ratio of approximately 5.0. In REM sleep state, a healthy patient has an LF/HF ratio of approximately 3 whereas a post-myocardial infarction patient has an LF/HF ratio of approximately 9.

Because of the relationship between the heart rate variability LF/HF ratio and sleep state, a determination of sleep state can be made by monitoring heart rate variability. The system of the invention, in at least one embodiment, does just that.

Figure 4A:
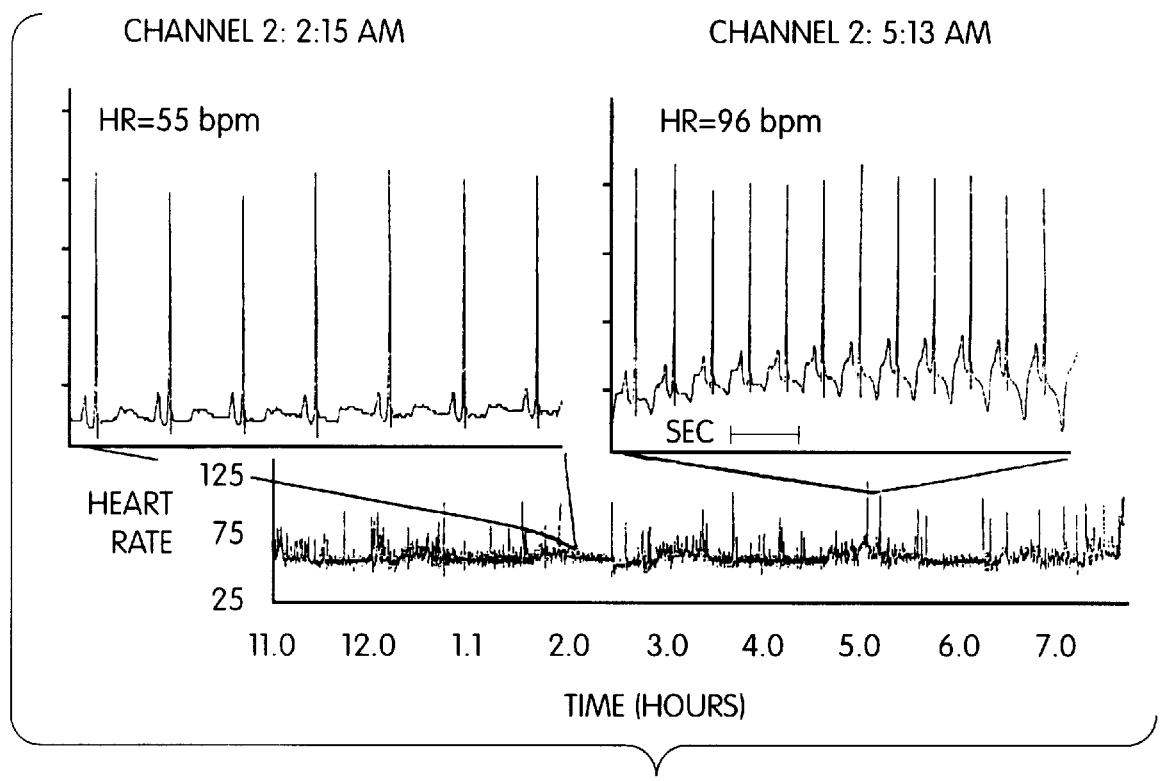
FIG. 4 is a graph illustrating a relationship between heart rate and eyelid movement frequency during sleep.
Figure 4B:
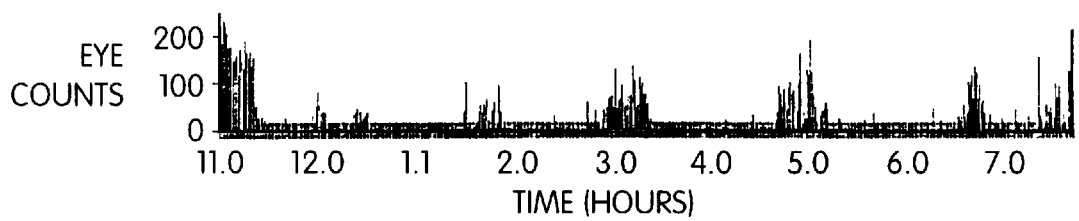

FIG. 4 is a graph illustrating the relationship between heart rate and frequency of eyelid movements during sleep. This relationship provides a basis for diagnosing heart related abnormalities during sleep, as will be described in greater detail below. The goal of simultaneous recording of sleep state and ECG is to identify sleep-state dependent triggers of ECG abnormalities, including rhythm and blood flow to the heart muscle. Only recently has the extent of the impact of normal sleep on the occurrence of major cardiac events including myocardial infarction and sudden cardiac death been studied as well as the potential triggering of such events by the central nervous system. The non-random distribution of the approximately 300,000 myocardial infarctions and 37,500 sudden deaths which occur annually at night indicates changes in central and autonomic nervous system activity during different sleep states are a precipitating factor in a large number of these events.

Figure 5:
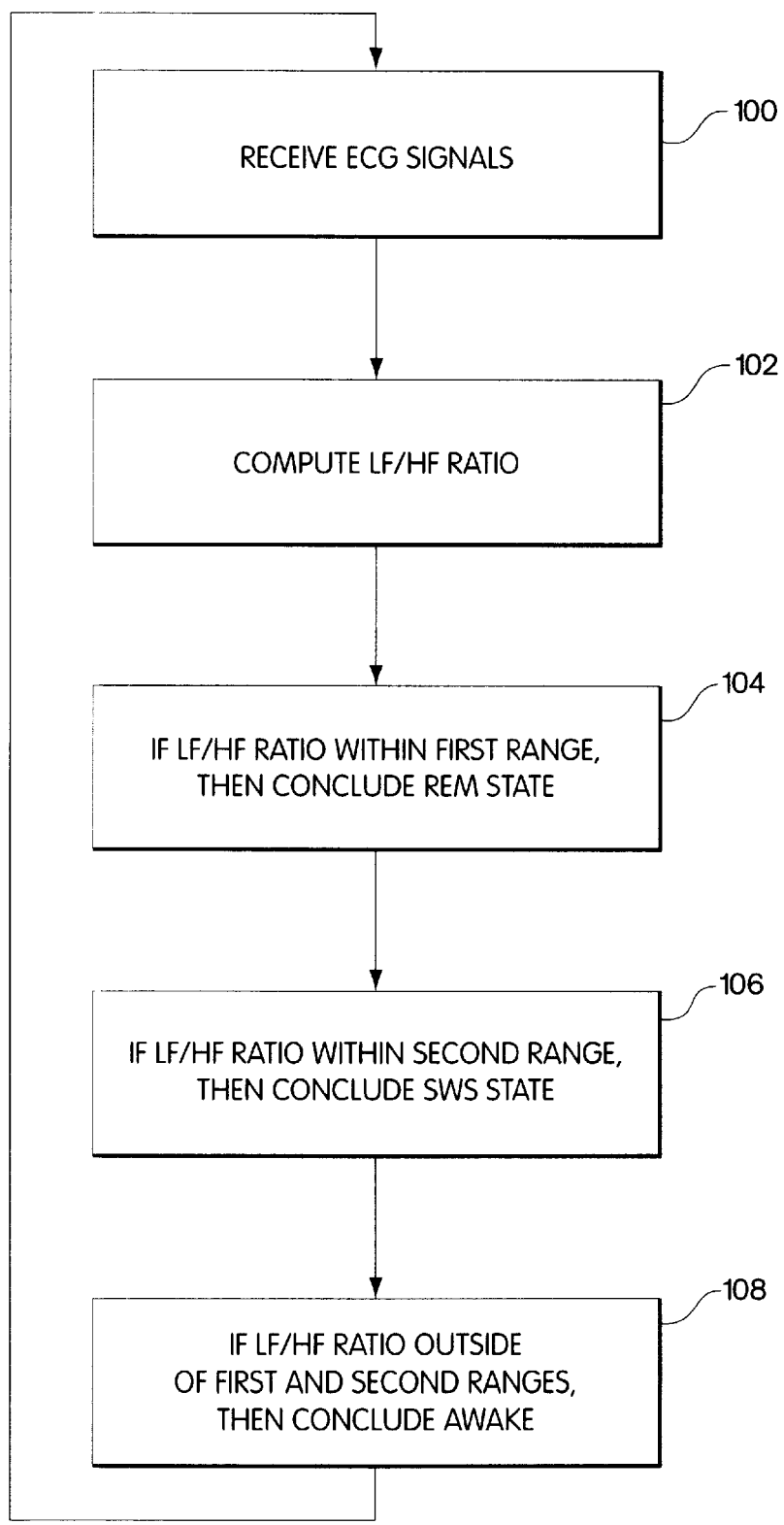
FIG. 5 is a flow diagram of the steps carried out by the processor in monitoring sleep state according to one embodiment of the invention.

FIG. 5 is a flow diagram showing the steps implemented by processor 34 in one embodiment of the invention in which sleep states are determined based on ECG signals. As shown, the process starts at step 100 where the ECG signals are received. Such signals are received on line 24 by synchronization circuit 30 (FIG. 2). The process then continues at step 102 where the LF/HF heart rate variability ratio is computed. This computation can be done continuously on an analog input signal or periodically at regularly spaced temporal intervals. At step 104, the processor analyzes the LF/HF ratio and determines whether it falls within a first predetermined range. If the LF/HF ratio does fall within the first predetermined range, then the processor concludes that the patient is in REM sleep state. If the LF/HF ratio does not fall within the first predetermined range, then, at step 106, the processor analyzes the LF/HF ratio to determine whether it falls within a second predetermined range. If the LF/HF ratio does fall within the second predetermined range, then the processor concludes that the patient is in SWS sleep state. If the LF/HF ratio does not fall within either of the first predetermined range or the second predetermined range, then the processor concludes that the patient is in quiet wakefulness, at step 108. This process may be a repetitive (continuous) process.

It should be understood that the first predetermined range and the second predetermined range may be selected on a per-patient basis based on knowledge of each patient's sleeping habits and health. Different ranges would be selected for healthy patients than for patients who have heart ailment histories (i.e., those who have suffered myocardial infarctions). Each range can be open-ended (i.e., greater than a certain ratio or less than a certain ratio) or may be closed on both ends (i.e., greater than a certain ratio and less than a certain ratio).

Examples of particular LF/HF ratios for healthy patients and those with heart ailments are listed in the table below. These ranges listed are exemplary and in no way limiting. The ranges can be altered at any time when relevant information on the patient is learned.

| LF/HF RATIO RANGES | | |
|---|---|---|
| | HEALTHY | POST M.I. |
| REM | 3.04 +/− 0.74 | 8.9 +/− 1.63 |
| NON-REM | 1.22 +/− 0.33 | 5.11 +/− 1.34 |

As discussed above, the frequency of head movements, the frequency of eyelid movements, and LF/HF ratio all are related to sleep state. In accordance with another embodiment of the invention, the processor monitors sleep state based on all of this information. Very accurate monitoring therefore results.

Figure 6:
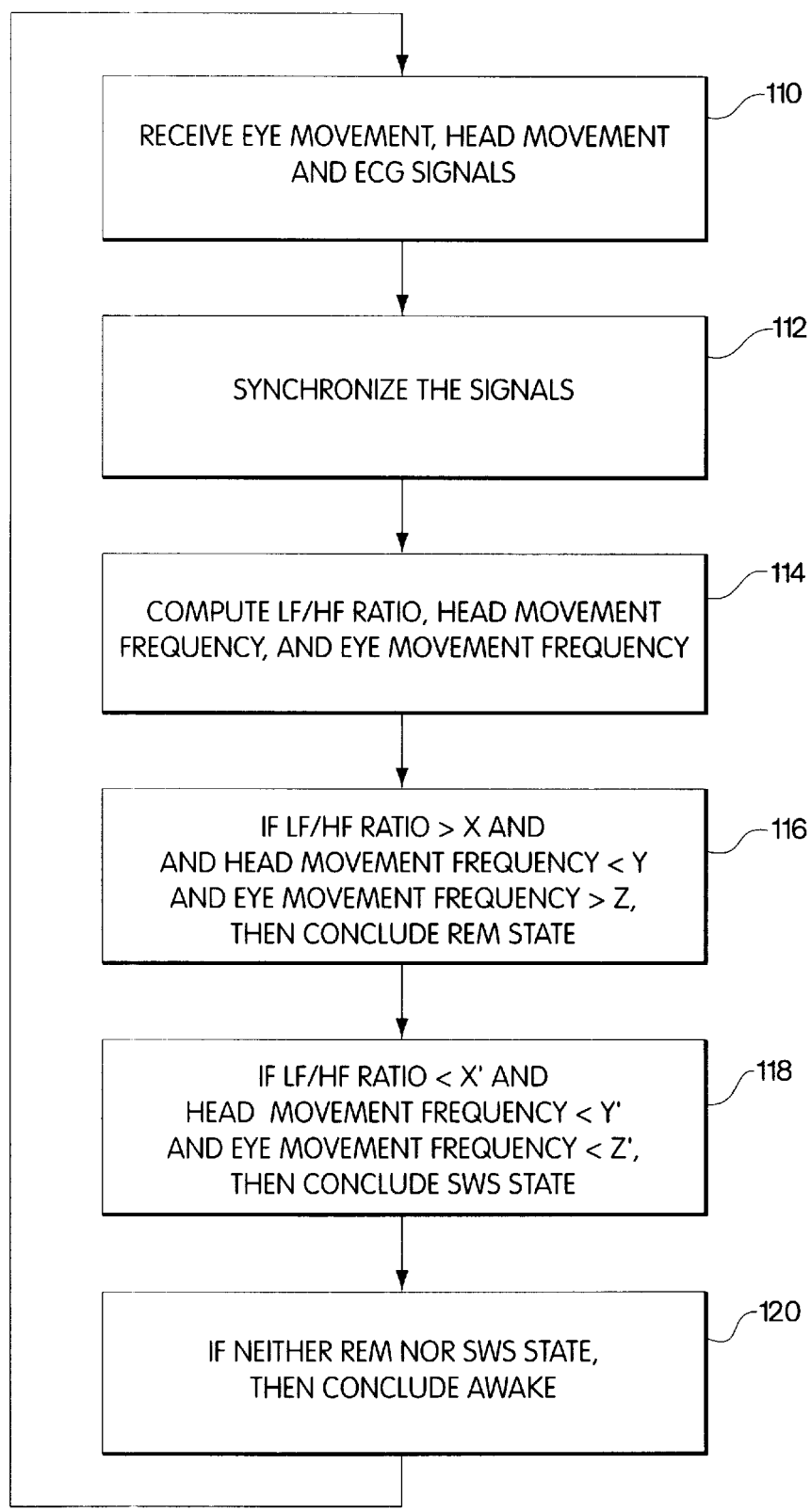
FIG. 6 is a flow diagram of the steps carried out by the processor in monitoring sleep state according to another embodiment of the invention.
Figure 7A:
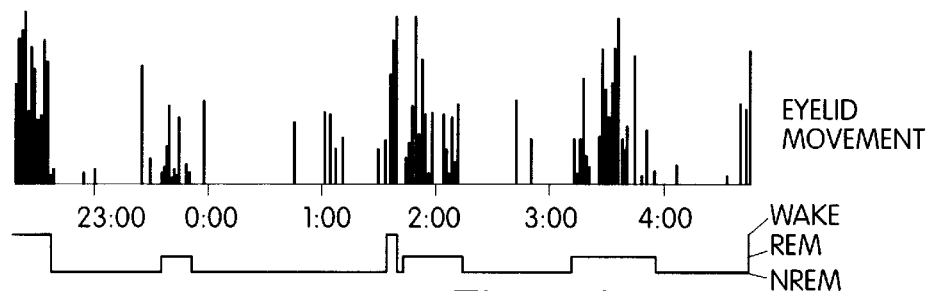
FIGS. 7A–7D are graphs illustrating a relationship between eyelid movement frequency and breathing disorders.
Figure 7B:
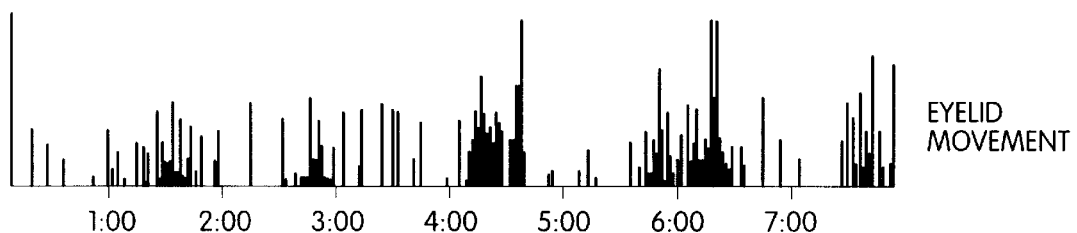
Figure 7C:
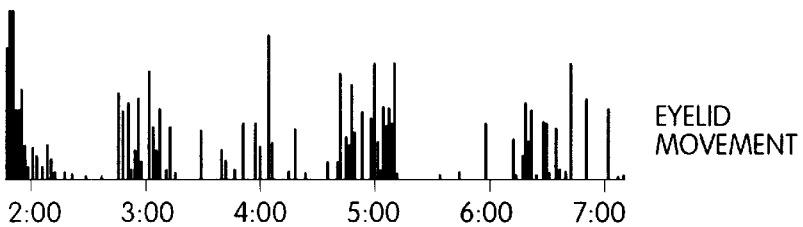
Figure 7D:
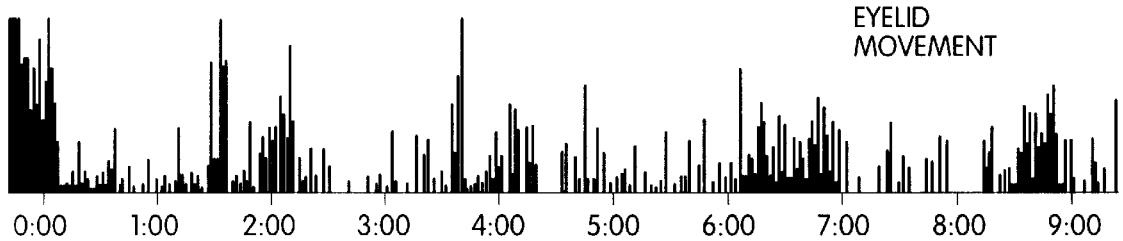

The steps of the scheme implemented by the processor in this embodiment are shown in FIG. 6. As shown, the processor begins at step 110 by receiving eyelid movement, head movement and ECG signals. At step 112, the signals are synchronized. At step 114, the LF/HF ratio, frequency of head movements and frequency of eyelid movements are computed.

At step 116, the processor determines whether the LF/HF ratio is greater than a predetermined number X, whether the head movement frequency is less than a predetermined number Y, and whether the eyelid movement frequency is greater than a predetermined number Z. If so, then processor concludes that the patient is in REM state. If not, then at step 118, the processor determines whether the LF/HF ratio is less than a predetermined number X', whether the head movement frequency is less than a predetermined number Y', and whether the eyelid movement frequency is less than a predetermined number Z'. If so, then the processor concludes that the patient is in SWS state. If none of the criteria within steps 116 and 118 is met, then the processor concludes that the patient is in quiet wakefulness.

Like with the embodiment of FIG. 5, the predetermined numbers, X, X', Y, Y', Z and Z' may be selected on a per-patient basis with knowledge of the patient's sleeping habits and health history. The numbers can be altered at any time. Additionally, while the comparisons are shown as open ended (i.e., greater than or less than a certain number), such comparisons alternatively can be performed to see whether the LF/HF ratio, head movement frequency or eyelid movement frequency is within a certain range.

Examples of the predetermined numbers Y, Y', Z and Z' may be based on the following simple example. REM state is concluded if there exists eyelid movement and no head movement. SWS state is concluded if there exists no eyelid movement and no head movement. Wakefulness is concluded if there exists head movement and no eyelid movement. More complex schemes may be developed with the system and method of the invention.

FIGS. 7A–7D are graphs showing the relationship between the frequency of eyelid movements and certain breathing disorders. As shown, the frequency of eyelid movements increases as the severity of the breathing-disordered sleep increases. The system of the invention will be able to distinguish patients with severe sleep-disordered breathing, who are found to experience approximately 85 eyelid movements/minute, from normal individuals, who are found to experience approximately 167 eyelid movements/minute, from individuals with mild or moderate sleep-disordered breathing, who respectively are found to experience approximately 169 or 164 eyelid movements/minute.

In an embodiment of the invention, the breathing pattern of a patient is monitored by examining the strength of ECG signals received from the ECG electrodes. During inspiration, as the chest wall expands, the ECG electrodes (16A–16E of FIG. 1) move further from the heart. As this occurs, the magnitude of the ECG signals received lessens. During expiration, the chest wall contracts bringing the ECG electrodes closer to the heart. During expiration, therefore, the ECG signals grow in magnitude. This phenomena in chest wall expansion and contraction is referred to as chest wall impedance or resistivity.

Figure 8:
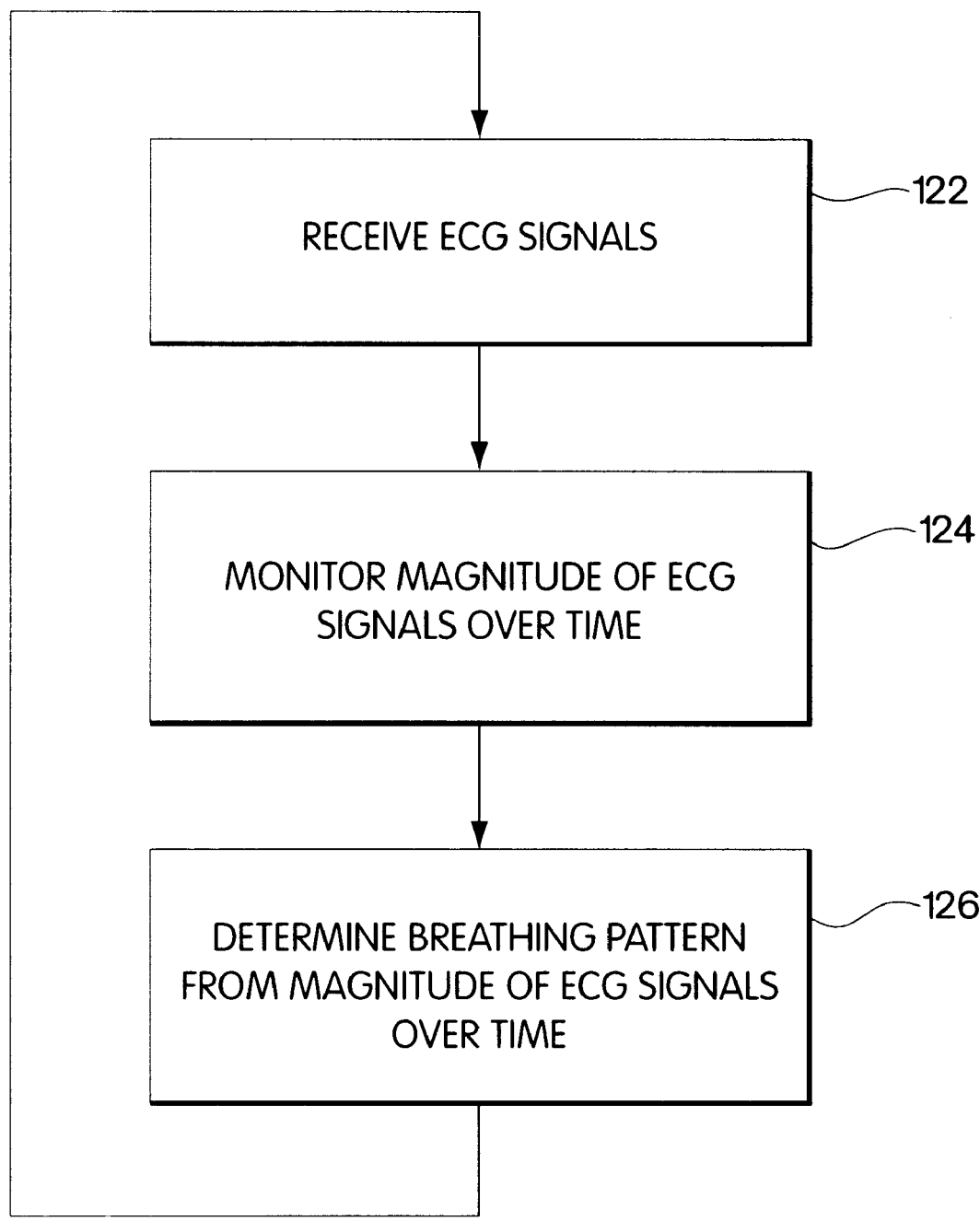
FIG. 8 is a flow diagram of steps carried out by the processor in monitoring breathing rhythm according to one embodiment of the invention.
Figure 9:
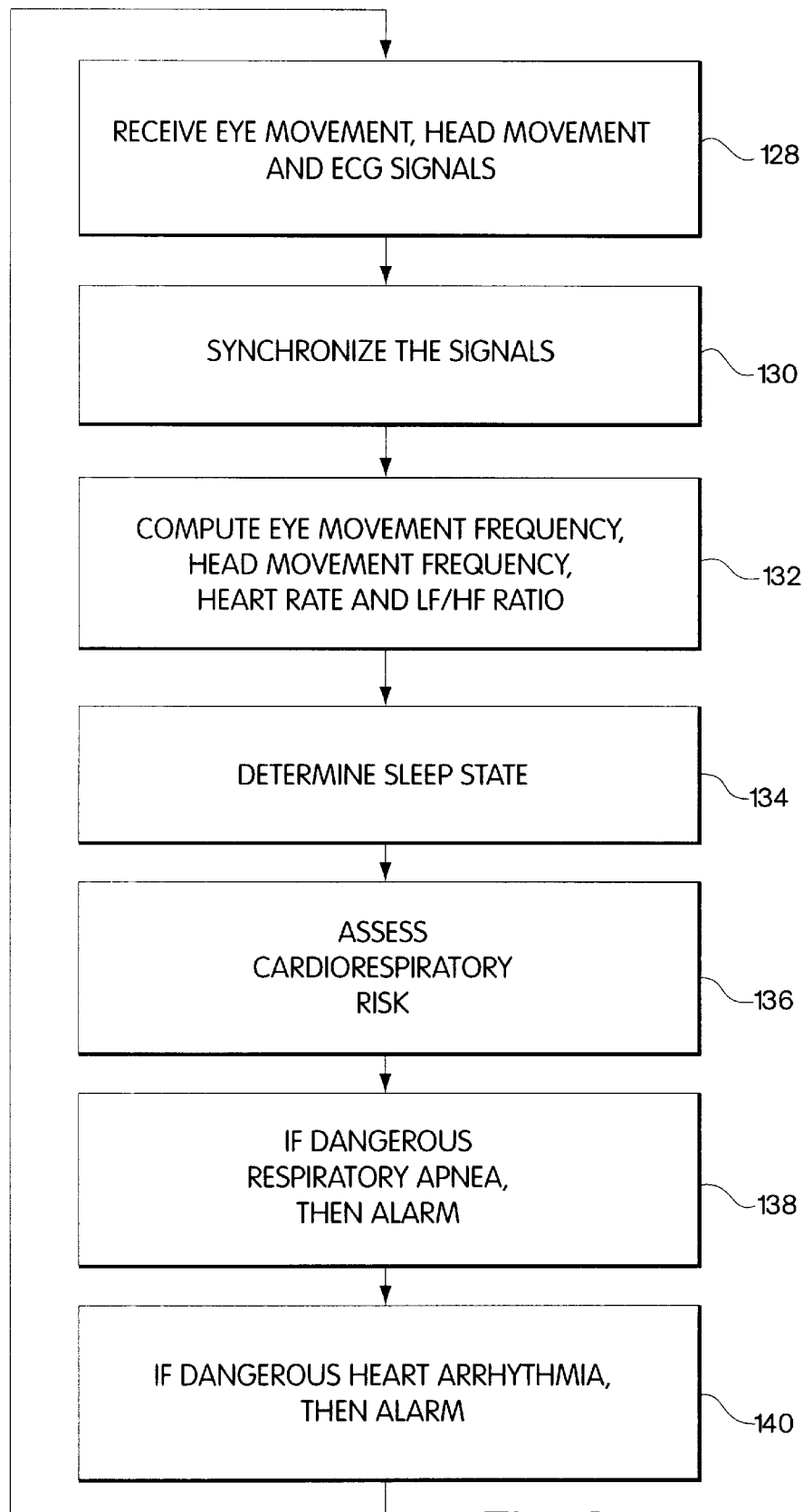
FIG. 9 is a flow diagram of steps carried out by the processor in monitoring sleep state, breathing rhythm and heart function according to one embodiment of the invention.

By continuously monitoring the magnitude of the ECG signals, which should have a sine wave pattern (each period corresponding to one inspiration and one expiration) during normal breathing, the system of the invention can monitor breathing pattern and rate. FIG. 8 is a flow diagram showing the steps carried out by the processor when monitoring breathing pattern. As shown, at step 122, the ECG signals are received. At step 124, the magnitude of the ECG signals are monitored over time. At step 126, the breathing pattern is determined from the magnitude of the ECG signals over time. This process is a repetitive and continuous one.

In one embodiment of the invention, the system, through receipt of eyelid movement, head movement and ECG signals, monitors sleep state, breathing pattern and heart function, and provides alarm signals when dangerous respiratory apneas and/or heart arrhythmias are detected. The steps carried out by the processor in this embodiment are shown in the flow diagram of FIG. 9. As shown, at step 128, eyelid movement, head movement and ECG signals are received. At step 130, the signals are synchronized temporally. At step 132, eyelid movement frequency, head movement frequency, heart rate and LF/HF ratios are computed. In step 134, sleep state is determined. It may be determined in accordance with either of the schemes of FIGS. 5 and 6.

At step 136, cardiorespiratory risk is assessed. The assessment is done on a per-patient basis and will evolve as more is learned about the relationship between sleep state, heart function and cardiac and respiratory ailments and dangerous events. At step 138, if a dangerous breathing apnea is detected, then an alarm is issued to awaken the patient. At step 140, if a dangerous heart arrhythmia is detected, then an alarm is issued to awaken the patient.

The processor may also analyze the received signals to asses cardiorespiratory risk and diagnose disorders. A respiratory disorder (i.e., apnea) may, for example, be diagnosed from the frequency of eyelid movements and/or from the ECG signals R-wave amplitude and pattern (used to determine respiratory pattern). Cardiac disorders (such as cardiac arrhythmia or myocardial ischemia) known to be linked to certain respiratory disorders also may be inferred upon detection of such respiratory disorders. This information may be preprogrammed. As another example, sleep-related cardiac risk (i.e., arrhythmia) and/or respiratory risk due to autonomic and/or central nervous system activity may be detected based on ECG signals RR-segment (if related to heart rate variability) and/or based on sleep state determinations (i.e., if a patient is known to be at risk in REM state). In addition, the analysis of the received signals may help define the autonomic basis and/or nervous system basis for sleep-related arrhythmogenesis, ischemia or respiratory disorder.

The system also may be used to monitor patients or to conduct studies to learn more about certain disorders and to learn more about the link between cardiac events, respiratory disorders and sleep states. The following questions may, for example, be answerable by the system of the invention. (1) Are cardiac or central nervous system medications affecting sleep-related arrhythmogenesis, myocardial ischemia, or sleep quality? (2) Is the cardiac patient being medicated properly given the decreased blood pressure that occurs during SWS state and the increased central nervous system activity that occurs during REM state? (3) Do respiratory disorders contribute to the risk of dangerous cardiac events? (4) Are cardiac patients' arrhythmias and ischemia being triggered by sleep-state dependent activity (such as central nervous system activity)? (5) What is the basis/origin (central nervous system or other) of patients' apneas? (6) Based on the known link between exhaustion and an increased risk of myocardial infarction, are cardiac patients' exhaustion due to cardiac factors, poor sleep, and/or disrupted respiration? (7) Based on the presently unknown pathological bases for SIDS and SUNDS, is/are the root cause(s) found to be in the cardiac system, the respiratory system, and/or the central nervous system? (8) Is atrial fibrillation being triggered by sleep-state phenomena?

The system of the invention has tremendous utility in many applications. It is a home-based system that can be used fairly easily by a patient after a patient is released from the hospital. As discussed, the system also can be used to diagnose whether a patient has a dangerous sleep-triggered condition, such as a heart and/or breathing irregularity.

Oftentimes, when a patient is released from the hospital after a myocardial infarction or myocardial ischemia, or other heart and/or breathing-related ailment, there is no simple way to monitor the health of the patient. These patients typically are at high risk for recurrences of heart and/or breathing-related events (such as arrhythmias, apneas and/or myocardial infarctions). The system and method of the invention provides a mechanism by which a patient can be self-monitored at home after release from the hospital.

The system and method also is particularly useful in determining the effects during sleep of heart-related drugs issued to patients with heart ailments. The system of the invention will monitor heart function and sleep state and will provide an indication of how certain medicines (particularly those that cross the brain-blood barrier) affect heart function during sleep.

Another very important feature of the system and method of the invention is that an automatic alarm system is included for awakening a patient should a dangerous breathing or heart-related event occur. In the past, heart-ailment patients would have to rely on self-alarming (such as being awakened by a dream) for such purpose. Foreseeable medical applications are delineated in Verrier and Hobson, "Sleep-Related Cardiovascular Risk", published by Futura in Annals of *Noninvasive Electrophysiology*, April, 1997, which is herein incorporated by reference.

Examples of conditions for which the system and method of the invention are particularly useful are listed below. The list is non-exclusive.

1. Patients with spousal or family report of highly irregular breathing, excessive snoring or apnea in patients with coronary disease. Disturbed breathing may be investigated with the system and method of the invention in the familiar home environment for the presence of apnea, a condition which may exacerbate ischemic events and lead to arrhythmia, hypertension, infarction or sudden death.
2. Patients with pause-dependent Torsade de Pointes (drug induced or long QT3) syndrome. The profound cycle-length changes associated with sleep may trigger this arrhythmia. The system of the invention can help diagnose this syndrome and aid in the prevention of arrhythmias commonly associated with it.
3. Near-miss patients or siblings of SIDS victims. This "crib death" is the leading cause of death in infants between one week and one year of age and appears to be a sleep-related cardiorespiratory phenomenon. As such, the diagnostic opportunity provided by the system of the invention may aid in its prevention.
4. Asians with warning signs of SUNDS. SUNDS is a sleep-related phenomenon attacking seemingly healthy individuals in which night terrors may play a role. Accordingly, the system of the invention may aid in diagnosing and/or saving the lives of such patients.
5. Patients on cardiac medications which cross the blood-brain barrier. Beta blockers and calcium channel blockers may increase the risk of nighttime cardiac events, as poor sleep and violent dreams may be triggered. Therefore, the system of the invention can play a role in helping select an appropriate medicine and dosage and in saving the lives of those with life-threatening nocturnal heart arrhythmias.
6. Patients with hypertension. Sleep apnea is an established risk factor for systemic hypertension independent of the influence of age and obesity. This condition accordingly can be monitored with the system of the invention and its risks can be minimized.
7. Patients with nocturnal ischemic heart disease, angina and arrhythmias. Most episodes of ischemia in patients with stable coronary disease are due to increases in myocardial oxygen demand and only approximately 8–10% of ischemic attacks and angina occur during sleep. The majority of ventricular arrhythmias occurring during the nocturnal period, however, do so during REM sleep. This may be due to surges in autonomic activity during REM. By providing a better guide to pharmacologic management, the system of the invention may aid in saving lives.
8. Patients who have suffered myocardial infarctions. These patients are particularly at risk during sleep because normal sleep activates the autonomic nervous system and may disrupt breathing or myocardial perfusion. As such, the system of the invention may save their lives.
9. Patients at risk for paroxysmal atrial fibrillation. This arrhythmia, which can result in morbidity and mortality, has greater nighttime than daytime occurrence, but its sleep-state dependency is not known.
10. Patients in heart failure, particularly those with existing respiratory disorder, a combination which may provoke Cheyne-Stokes respiration. The alarm feature would be particularly valuable for patients in advanced heart failure.
11. Patients on non-cardiac medications. These should be screened for proarrhythmic effects and for disruption of sleep or respiration, as the potential exists for both direct and indirect effects on the central nervous system, the cardiovascular system, and the respiratory system.

Patients in all of the above categories are high-risk patients for nighttime events and would most benefit from the home-based system and method of the invention. The sleep-state dependent nocturnal triggers of cardiac and respiratory vulnerability could be identified and the potential sleep disruptive affects of cardiac medications can be evaluated. More accurate treatment for cardiac patients is expected to result. Additionally, the alarm feature of the invention may save the lives of patients who otherwise would suffer while sleeping until death.

Having thus described at least one illustrative embodiment of the invention, various alterations, modifications and improvements will readily occur to those skilled in the art. Such alterations, modifications and improvements are intended to be within the spirit and scope of the invention. Accordingly, the foregoing description is by way of example only and is not intended as limiting. The invention is limited only as defined in the following claims and the equivalents thereto

What is claimed is:

1. A method of determining sleep states of a patient comprising the steps of:

monitoring a heart rate of the patient through receipt of heart beat signals;

monitoring a frequency of eyelid movements of the patient through receipt of eyelid signals; and monitoring a frequency of head movements of the patient through receipt of head signals;

using a single, wearable, self-contained processing system, temporally synchronizing and processing the heart beat signals, eyelid signals and head signals to determine the sleep state of the patient and to assess cardiorespiratory risk.

2. The method claimed in claim 1 wherein step of monitoring the frequency of eyelid movements includes applying an eyelid sensor the eyelid of the patient which eyelid sensor produces an eyelid signal each time the eyelid moves.

3. The method claimed in claim 2 wherein step of monitoring heart rate includes applying at least one heart sensor to a chest wall of the patient, which heart sensor produces a heart beat signal each time the heart beats.

4. A home-based, self-contained, wearable processing system comprising:

an eyelid sensor adapted to be applied to an eyelid of the patient to produce eyelid signals representing eyelid movements;

a head movement sensor adapted to be applied to the head of the patient to produce head signals representing head movements;

at least one heart sensor adapted to be applied to the chest wall of the patient to produce heart beat signals representing heart beats; and a processor that temporally synchronizes, records and analyzes the eyelid, head and heart beat signals to assess cardiorespiratory risk.

5. The system claimed in claim 4 wherein the processor also determines a sleep state of the patient based on the eyelid, head and heart beat signals.

6. The system claimed in claim 4 wherein the processor also determines a breathing pattern of the patient based on the heart beat signals.

7. The system claimed in claim 4 further including an alarm coupled to the processor, that is triggered to produce an alarm signal when a dangerous cardiorespiratory state is detected.

* * * * *

UNITED STATES PATENT AND TRADEMARK OFFICE

CERTIFICATE OF CORRECTION

PATENT NO. : 5,902,250

DATED : May 11, 1999

INVENTOR(S): Richard L. Verrier, J. Allan Hobson, Eric G. Lovett and Edward F. Pace-Schott It is certified that error appears in the above-identified patent and that said Letters Patent is hereby corrected as shown below:

Column 1, line 5

--This invention was supported by the National Institutes of Health, Grant Nos. MH13923 and HL50078 and the government has certain rights to this invention.--

IN THE CLAIMS

Column 15, line 3, after "eyelid sensor", please add --to--.